United States Patent [19]

Lee et al.

[11] 4,358,606

[45] Nov. 9, 1982

[54] ESTERS OF PHENALKYLOXYCARBONYLAMINO ACIDS

[75] Inventors: Shy-Fuh Lee, Sunnyvale; Clive A. Henrick, Palo Alto, both of Calif.

[73] Assignee: Zoecon Corporation, Palo Alto, Calif.

[21] Appl. No.: 275,099

[22] Filed: Jun. 19, 1981

[51] Int. Cl.³ ..................................... C07C 125/065
[52] U.S. Cl. ................................. 560/163; 546/331;
546/332; 560/34; 546/335; 546/336; 560/135;
546/337; 560/9; 560/137; 560/21; 560/22;
560/159; 560/27; 560/29; 560/164; 560/31;
560/32; 560/169; 564/48; 564/49; 564/52;
564/53; 564/54; 564/56; 71/94; 71/98; 71/100;
71/105; 71/106; 71/107; 71/111; 71/112;
71/119; 71/120; 260/455 R; 260/455 A;
260/465 D; 260/463; 542/416; 546/292;
546/296; 546/306; 546/309; 546/330
[58] Field of Search ................. 260/402.5, 404, 404.5,
260/465 D, 455 R; 560/9, 21, 22, 27, 29, 31, 32,
135, 137, 142, 145, 163, 159

[56] References Cited

U.S. PATENT DOCUMENTS

| 3,235,357 | 2/1966 | Loux | 71/81 |
| 3,340,294 | 9/1967 | Richter | 560/163 |
| 3,399,048 | 8/1968 | Herrett | 560/163 |
| 3,399,228 | 8/1968 | Herrett | 560/163 |

OTHER PUBLICATIONS

MacDonald, J. Med. Chem., 23 pp. 413-420.
Kricheldorf, Angew. Chem., Int. Ed. Engl., 11, pp. 128-129 (1972).

*Primary Examiner*—Michael L. Shippen
*Attorney, Agent, or Firm*—Jacqueline S. Larson; Donald W. Erickson; Thomas T. Gordon

[57] ABSTRACT

Novel esters of phenylalkyloxy- or phenylalkylthioacylamino acids and pyridylalkyloxy- or pyridylalkylthioacylamino acids, synthesis thereof, intermediates therefor, and the use of said esters for the control of weeds.

10 Claims, No Drawings

ESTERS OF PHENALKYLOXYCARBONYLAMINO ACIDS

The present invention relates to novel esters of phenylalkyloxy- or phenylalkylthioacylamino acids and pyridylalkyloxy- or pyridylalkylthioacylamino acids, synthesis thereof, intermediates therefor, and the use of said esters for the control of weeds.

More particularly, the novel compounds of the present invention are represented by the following formula (A):

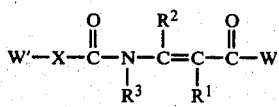
(A)

wherein,

W is lower alkyl, aryl, OR, SR, NHR or N(R)$_2$;

R is lower alkyl, lower alkenyl, phenyl, substituted phenyl, phenylalkyl or lower haloalkyl;

R$^1$ is hydrogen, lower alkyl, halogen, acyl, phenylacyl, substituted phenylacyl, phenyl substituted phenyl or

R$^2$ is hydrogen, lower alkyl, lower haloalkyl, phenyl or substituted phenyl;

R$^3$ is hydrogen or lower alkyl;

X is oxygen, sulfur or the group

W' is the group

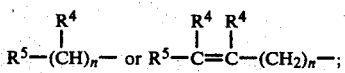

n is zero, one, two, three, four or five;

R$^4$ is hydrogen, lower alkyl, lower haloalkyl or halogen; and

R$^5$ is the group

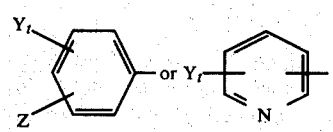

where t is zero, one, two, three or four; Y is halogen, lower alkyl, lower haloalkyl, lower haloalkoxy or lower haloalkylthio; and Z is hydrogen or independently selected from the values of Y.

The compounds of formula (A) are effective herbicidal agents, particularly as post-emergent herbicides against grasses and broad-leaved plants, and plant growth regulators.

Synthesis of the compounds of formula (A) may be outlined as follows:

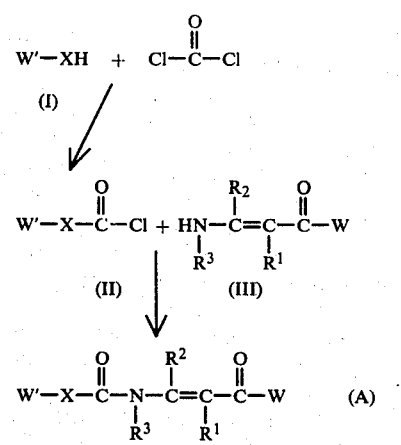

In the above synthesis, an alcohol or thiol of formula (I) is reacted with phosgene in the presence of an organic solvent such as toluene. The resulting chloroformate or thiocarbonyl chloride (II) and an amino alkenoic acid ester, thioester or amide (III) are combined in the presence of an organic solvent such as ether or methylene chloride with or without base to produce the compounds of the present invention.

The following terms, wherever used in the description herein and in the appended claims, have the meaning defined below, unless otherwise specified hereinafter.

The term "lower alkyl" refers to an alkyl group, straight or branched, having a chain length of one to eight carbon atoms. The term "lower haloalkyl" refers to a lower alkyl group substituted with one to three halogen atoms.

The term "lower alkenyl" refers to an alkenyl group, straight or branched, having a chain length of two to eight carbon atoms and one or two ethylenic bonds.

The term "lower haloalkoxy" refers to a lower alkoxy group having a chain length of one to eight carbon atoms substituted with one to three halogen atoms.

The term "lower haloalkylthio" refers to an alkylthio group, straight or branched, having a chain length of one to eight carbon atoms substituted with one to three halogen atoms.

The term "phenylalkyl" refers to a lower alkyl group in which a hydrogen atom of the alkyl group is substituted by phenyl, the total number of carbon atoms being from seven to twelve.

The term "acyl" refers to a lower acyl group of one to six carbon atoms. The term "phenylacyl" refers to a lower acyl group in which a hydrogen atom of the acyl group is substituted by phenyl, the total number of carbon atoms being from seven to twelve. The terms "substituted phenyl" or "substituted phenylacyl" refer to a phenyl group or a phenylacyl group substituted at one, two or three of the ring carbon atoms with a group selected from lower alkyl, lower haloalkyl, lower haloalkoxy, lower haloalkylthio, halogen, cyano or nitro.

The novel compounds of formula (A) are useful for the control of weeds, particularly using post-emergent treatments. The compounds can be applied in the form of dusts, granules, solutions, emulsions, wettable powders, flowables and suspensions. Application of a compound of the present invention is made according to conventional procedure to the weeds or their locus using an herbicidally effective amount of the compounds, usually from about one-half to ten pounds per acre.

Methods of preparing herbicidal formulations which can be used with a compound of the present invention are known in the art. In the preparation of the herbicidal compositions, a compound of the present invention can be uniformly mixed with or dissolved in suitable adjuvants such as a solid carrier, for example talc, clay, kaolin, diatomaceous earth or silica gel; a liquid carrier, for example alcohols, dioxane, acetone, methyl naphthalene or dimethylformamide; surfactants as emulsifiers, dispersing agents or wetting agents, for example alkyl sulfate, alkyl sulfonate, polyoxyethyleneglycol ethers or polyoxyethylenealkylaryl ethers; and carboxymethyl cellulose, gum arabic and other adjuvants.

The compounds of the present invention have a broad spectrum of herbicidal activity, being effective on both broad-leaf plants and the grassy weeds or graminaceous weeds. The optimum usage of a compound of the present invention is readily determinable by one of ordinary skill in the art using routine testing such as greenhouse testing and small plot testing.

The following examples are provided to illustrate the practice of the present invention. Temperature is given in degrees Centigrade. "RT" means room temperature.

EXAMPLE 1

A mixture of benzyl chloroformate (2.0 g) and ethyl 3-amino-2-butenoate (ethyl β-aminocrotonate) (1.48 g, 1.2 eq.) in 20 ml of methylene chloride is stirred overnight at RT. The reaction mixture is then diluted with methylene chloride, washed with water, dried and evaporated to dryness. Purification by preparative thin layer chromatography (TLC) gives ethyl 3-benzyloxycarbonylamino-2-butenoate, M/e (M+ 263).

EXAMPLE 2

A mixture of 3,4-dichlorobenzyl alcohol (2.0 g) and phosgene (2.35 g) in toluene (12 ml) is stirred at RT for 6 hours. Toluene is removed in vacuo, leaving 3,4-dichlorobenzyl chloroformate which is combined with ethyl 3-amino-2-butenoate (1.74 g) in methylene chloride (15 ml). After stirring at RT overnight, the reaction mixture is concentrated and purified by prep. TLC (silica gel) to give ethyl 3-(3,4 dichlorobenzyloxycarbonylamino)-2-butenoate, m.p.=83.5°–85°.

EXAMPLE 3

Following the procedure of Example 2, 4-chlorobenzenethiol (1.47 g) and phosgene (1.9 g) in toluene (9 ml) are reacted together, giving S-4-chlorobenzyl thiocarbonyl chloride. The thiocarbonyl chloride in 10 ml of methylene chloride is reacted with ethyl 3-amino-2-butenoate to yield ethyl 3-(S-4-chlorobenzyl-thiocarbonylamino)-2-butenoate, M/e (M+ 313).

EXAMPLE 4

Following the procedure of Example 2, 3-trifluoromethylbenzyl chloroformate is prepared from 3-trifluoromethylbenzyl alcohol (2.0 g) and phosgene (2.24 g) in toluene (10 ml). The chloroformate in ether (10 ml) is reacted with ethyl 3-amino-2-butenoate (2.9 g) in methylene chloride (20 ml) to give, after filtration, concentration and purification, ethyl 3-(3-trifluoromethylbenzyloxycarbonylamino)-2-butenoate, M/e (M+ 331).

In the same manner, each of the chloroformates in column I, prepared from the corresponding alcohol, is reacted with ethyl 3-amino-2-butenoate to give the final product in column II.

I 3-chloro-4-trifluoromethylbenzyl chloroformate
4-chlorobenzyl chloroformate
3.methylbenzyl chloroformate
4-difluoromethoxybenzyl chloroformate
3-trifluoromethylthiobenzyl chloroformate
3-bromobenzyl chloroformate
3,4,5-trichlorobenzyl chloroformate
4-chloro-3-trifluoromethylbenzyl chloroformate

II ethyl 3-(3-chloro-4-trifluoromethylbenzyloxycarbonylamino)-2-butenoate
ethyl 3-(4-chlorobenzyloxycarbonylamino)-2-butenoate
ethyl 3-(3-methylbenzyloxycarbonylamino)-2-butenoate
ethyl 3-(4-difluoromethoxybenzyloxycarbonylamino)-2-butenoate
ethyl 3-(3-trifluoromethylthiobenzyloxycarbonylamino)-2-butenoate
ethyl 3-(3-bromobenzyloxycarbonylamino)-2-butenoate
ethyl 3-(3,4,5-trichlorobenzyloxycarbonylamino)-2-butenoate
ethyl 3-(4-chloro-3trifluoromethybenzyloxycarbonylamino)-2-butenoate

EXAMPLE 5

Following the procedure of Example 3, each of the thiocarbonyl chlorides in column III, prepared from the corresponding thiol, is reacted with 3-amino-2-butenoate to give the final product in column IV.

III benzyl thiocarbonyl chloride
3,4-dichlorobenzyl thiocarbonyl chloride
3-chloro-4-trifluoromethylbenzyl thiocarbonyl chloride
3,4,5-trichlorobenzyl thiocarbonyl chloride

IV ethyl 3-(benzylthiocarbonylamino)-2-butenoate
ethyl 3-(3,4-dichlorobenzylthiocarbonylamino)-2-butenoate
ethyl 3-(3-chloro-4-trifluoromethylbenzylthiocarbonylamino)-2-butenoate
ethyl 3-(3,4,5-trichlorobenzylthiocarbonylamino)-2-butenoate

EXAMPLE 6

Phenyl bromide (23.5 ml, 0.225 mol) is slowly added along with 120 ml of ether to magnesium (5.7 g, 0.236 mol) covered with ether, and the reaction mixture is heated under reflux for 0.5 hour. To the resulting phenylmagnesium bromide in ether at 20°–25° is slowly added ethyl cyanoacetate (8.47 g, 0.075 mol) over 50 min. with stirring. After the addition, the reaction mixture is allowed to stand at RT overnight. It is then worked up by adding 37 ml of ammonium chloride, with cooling and vigorous stirring, followed by filtering the mixture and washing the solid with ether (2X). The combined ether filtrates are washed with water and with brine and dried. Filtration, rotoevaporation and distillation yield ethyl 3-amino-3-phenyl-2-propenoate.

Following the procedure of Example 2, each of ethyl 3-amino-3-phenyl-2-propenoate, ethyl 3-amino-2-propenate, ethyl 3-amino-2-pentenoate and ethyl 3-amino-5-chloro-2-pentenoate is reacted with 3,4-dichlorobenzyl chloroformate to give, respectively, ethyl 3-(3,4-dichlorobenzyloxycarbonylamino)-3-phenyl-2-propenoate, ethyl 3-(3,4-dichlorobenzyloxycarbonylamino)-2-propenoate, ethyl 3-(3,4-dichlorobenzyloxycarbonylamino)-2-pentenoate and ethyl 3-(3,4-dichlorobenzyloxycarbonylamino)-5-chloro-2-pentenoate.

EXAMPLE 7

To a mixture of 5 g (38.0 mmol) of ethyl 3-amino-2-butenoate and 3.23 ml (39.9 mmol) of pyridine in 40 ml of ether and 12 ml of hexamethylphosphoric triamide, refluxing under nitrogen, is slowly added 2.84 ml (39.9 mmol) of acetyl chloride in 10 ml of ether over 35 min. Several drops of water are added to decompose excess acid chloride and the reaction mixture is stirred at RT for about 1 hour. It is then poured into ether and water, and 10% hydrocholoric acid is added until the solution is acidic. The aqueous layer is extracted with ether (3X). The combined organic layers are washed with water until neutral and with brine, dried over calcium sulfate, filtered and rotoevaporated. The crude product is purified by column chromotography (silica gel, gradient elution starting with 20% ethyl acetate/hexane and increasing polarity to 25% ether/25% ethyl acetate/50% hexane) to give 2-acetyl-3-amino-2-butenoate.

Following the procedure of Example 2, ethyl 2-acetyl-3-amino-2-butenoate and 4-chlorobenzyl chloroformate are reacted together, yielding ethyl 2-acetyl-3-(4-chlorobenzyloxycarbonylamino)-3-butenoate.

In the same manner, 4-chloro-3-trifluoromethylbenzyl chloroformate and ethyl 3-amino-2-ethoxycarbonyl-2-butenoate are reacted together to give ethyl 3-(4-chloro-3-trifluoromethylbenzyloxycarbonylamino)-2-ethoxycarbonyl-2-butenoate.

EXAMPLE 8

β-Methylene-β-propiolactone (25 mmol) and an excess of allyl alcohol (35 mmol) are combined at RT, with stirring for about 2 hours. After distillation, the resulting allyl 3-ketobutanoate is reacted with anhydrous ammonia (1 eq.) at RT to give allyl 3-amino-2-butenoate.

In the same way, benzyl 3-amino-2-butenoate and n-butyl 3-amino-2-butenthioate are prepared using benzyl alcohol and 1-butanethiol, respectively, rather than allyl alcohol as the starting material.

Phenyl 3-amino-2-butenthioate is prepared as above except that the starting material benzenethiol is first dissolved in toluene.

Following procedure of Example 2, each of allyl 3-amino-2-butenoate, benzyl 3-amino-2-butenoate, n-butyl 3-amino-2-butenthioate and phenyl 3-amino-2-butenthioate is reacted with 3,4-dichlorobenzyl chloroformate, yielding, respectively, allyl 3-(3,4-dichlorobenzyloxycarbonylamino)-2-butenoate, benzyl 3-(3,4-dichlorobenzyloxycarbonylamino)-2-butenoate, n-butyl 3-(3,4-dichloro-benzyloxycarbonylamino)-2-butenthioate and phenyl 3-(3,4-dichloro-benzyloxycarbonylamino)-2-butenthioate.

EXAMPLE 9

A solution of 4-chloroacetoacetanilide (1 g) in ethanol (10 ml) is heated to 40°, and ammonia gas is passed through. Removal of the solvent gives 3-amino-2-butenoic acid 4-chloroanilide. Following the procedure of Example 2, 3-amino-2-butenoic acid 4-chloroanilide is heated with 3,4-dichlorobenzyl chloroformate to yield 3-(3,4-dichlorobenzyloxycarbonylamino)-2-butenoic acid 4-chloroanilide.

EXAMPLE 10

Following the procedure of Example 2, 3,4-dichlorobenzyl chloroformate and an excess of ethyl 3-methylamino-2-butenoate are reacted, in methylene chloride, to yield ethyl 3-(3,4-dichlorobenzyloxycarbonyl-N-methylamino)-2-butenoate.

EXAMPLE 11

Following the procedure of Example 2, 4-amino-3-penten-2-one and 3,4-dichlorobenzyl chloroformate are reacted together to give 4-(3,4-dichlorobenzyloxycarbonylamino)-2-penten-2-one.

In the same manner, 4-(3,4-dichlorobenzyloxycarbonylamino)-4-phenyl-3-buten-2-one is prepared from 3,4-dichlorobenzyl chloroformate and 4-amino-4-phenyl-3-buten-2-one.

EXAMPLE 12

A solution of 3,4-dichlorobenzyl chloroformate (10 mmol) and N-methyl 3-aminocrotonamide (20 mmol) in chloroform (30 ml) is heated at reflux temperature for 6 hours. The solution is then concentrated and the product is isolated by fractional cystallization to give N-methyl 3-(3,4-dichlorobenzyloxycarbonylamino)-crotonamide.

In the same manner, N,N-dimethyl 3-(3,4-dichlorobenzyloxycarbonylamino)crotonamide is prepared from 3,4-dichlorobenzyl chloroformate and N,N-dimethyl 3-aminocrotonamide.

EXAMPLE 13

Following the procedure of Example 2, each of (1-aminoethylidene)-N,N'-dimethyl malondiamide and (1-aminoethylidene)-N,N,N',N'-tetramethyl malondiamide is reacted with 3,4-dichlorobenzyl chloroformate to yield N,N'-dimethyl [1-(3,4-dichlorobenzyloxycarbonylamino)ethylidene]malondiamide and N,N,N',N'-tetramethyl [1-(3,4-dichlorobenzyloxycarbonylamino)ethylidene]malondiamide, respectively.

(1-Aminoethylidene)-N,N'-dimethyl malondiamide and (1-aminoethylidene)-N,N,N',N'-tetramethyl malondiamide may be prepared by treatment of N,N'-dimethyl malondiamide and N,N,N',N'-tetramethyl malondiamide, respectively, with triethyl orthoacetate and a catalytic amount of sodium in ethanol, following a modification of the procedure described by Williams, *J. Chem. Soc.*, 3046 (1961) and McElvain et al., *J. Amer. Chem. Soc.*, 64:1831 (1942), to give (1-ethoxyethylidene)-N,N'-dimethyl malondiamide and (1-ethoxyethylidene)-N,N,N',N'-tetramethyl malondiamide, respectively, followed by treatment with concentrated ammonium hydroxide in ethanol.

EXAMPLE 14

A mixture of di-(S-ethyl)malonthioate (200 mmol), acetic anhydride (320 mmol) and sodium carbonate (240 mmol) in THF (250 ml) is heated at reflux temperature for 8 hours. After the THF is removed, the residue is dissolved in water, acidified and extracted with ether. The combined ether extracts are concentrated and distilled carefully to give di-(S-ethyl) acetylmalonthioate.

The acetylmalonthioate is treated with trimethyl orthoformate in the presence of a catalytic amount of AMBERLYST ® cation exchange resin, giving S-ethyl 2-(S-ethylthiocarbonyl)-3-methoxy-2-butenthioate which is converted into S-ethyl 2-(S-ethylthiocarbonyl)-3-amino-2-butenthioate by treatment with concentrated ammonium hydroxide in 95% ethanol at 30°–40°.

Following the procedure of Example 2, 3,4-dichlorobenzyl chloroformate and S-ethyl 2-(S-ethylthiocarbonyl)-3-amino-2-butenthioate are reacted together to yield S-ethyl 3-(3,4-dichlorobenzyloxycarbonylamino)-2-(S-ethylthiocarbonyl)-2-butenthioate.

AMBERLYST is a trademark of Rohm and Haas for a cation exchange resin with strong acidic, sulfonic functionality and a cation exchange capacity of approximately 4.9 meq/g.

EXAMPLE 15

Following the procedure of Example 2, 4-chloro-n-prop-α-enylbenzyl chloroformate is prepared from 4-chlorocinnamyl alcohol and phosgene. The chloroformate is then reacted with ethyl 3-amino-2-butenoate to yield ethyl 3-(4-chloro-n-prop-α-enylbenzyloxycarbonylamino)-2-butenoate.

EXAMPLE 16

Following the procedure of Example 1, α-chlorobenzyl chloroformate (1.55 g, 8.2 mmol) and ethyl 3-amino-2-butenoate (1.27 g, 9.8 mmol) are reacted to give ethyl 3-(α-chlorobenzyloxycarbonylamino)-2-butenoate.

In like manner, each of α-methylbenzyl chloroformate and α-trifluoromethylbenzyl chloroformate is reacted with ethyl 3-amino-2-butenoate to yield, respectively, ethyl 3-(α-methylbenzyloxycarbonylamino)-2-butenoate and ethyl 3-(α-trifluoromethyl-benzyloxycarbonylamino)-2-butenoate.

EXAMPLE 17

Following the procedure of Example 2, each of 3,4-dichloroethylbenzyl chloroformate, 3,4-dichloro-n-propylbenzyl chloroformate and 3,4-dichlorophenyl chloroformate is reacted with ethyl 3-amino-2-butenoate to yield, respectively, ethyl 3-(3,4-dichloroethylbenzyloxycarbonylamino)-2-butenoate, ethyl 3-(3,4-dichloro-n-propylbenzyloxycarbonylamino)-2-butenoate and ethyl 3-(3,4-dicholorophenoxycarbonylamino)-2-butenoate.

EXAMPLE 18

Following the procedure of Example 2, each of 4-pyridylmethyl chloroformate and 2-pyridylmethyl chloroformate is reacted with ethyl 3-amino-2-butenoate to give, respectively, ethyl 3-(4-pyridylmethyloxycarbonylamino)-2-butenoate and 3-(2-pyridylmethyloxycarbonylamino)-2-butenoate.

EXAMPLE 19

Following the procedure of Example 2, each of ethyl 3-amino-2-phenyl-2-butenoate and ethyl 3-amino-2-methyl-2-butenoate is reacted with 3,4-dichlorobenzyl chloroformate to prepare ethyl 3-(3,4-dichlorobenzyloxycarbonylamino)-2-phenyl-2-butenoate and ethyl 3-(3,4-dichlorobenzyloxycarbonylamino)-2-methyl-2-butenoate, respectively.

What is claimed is:

1. A compound of the following formula:

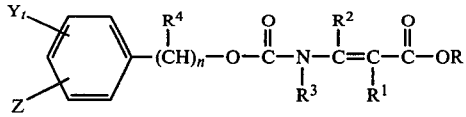

wherein, n is one, two, three, four or five;

R is lower alkyl, lower alkenyl or lower haloalkyl;

R¹ is hydrogen, lower alkyl, halogen,

phenyl, or phenyl substituted at one, two or three of the ring carbon atoms with a group selected from lower alkyl, lower haloalkyl, lower haloalkoxy, lower haloalkylthio, halogen, cyano and nitro;

R² is hydrogen, lower alkyl, lower haloalkyl, phenyl or phenyl substituted at one, two or three of the ring carbon atoms with a group selected from lower alkyl, lower haloalkyl, lower haloalkoxy, lower haloalkylthio, halogen, cyano and nitro;

R³ is hydrogen or lower alkyl;

R⁴ is hydrogen, lower alkyl, lower haloalkyl or halogen;

t is zero, one, two, three or four;

W is lower alkyl, phenyl, OR, SR, NHR or N(R)₂;

Y is halogen, lower alkyl, lower haloalkyl, lower haloalkoxy or lower haloalkylthio; and Z is hydrogen or independently selected from the values of Y.

2. A compound according to claim 1 wherein n is one, R is lower alkyl, R¹ is hydrogen or lower alkyl, R² is lower alkyl, R³ is hydrogen and R⁴ is hydrogen or lower alkyl.

3. A compound according to claim 2 wherein R is methyl or ethyl and R⁴ is hydrogen.

4. A compound according to claim 3 wherein R¹ is hydrogen and R² is methyl or ethyl.

5. A compound according to claim 4 wherein t is zero, one or two; Y is chloro, bromo or trifluoromethyl; and Z is hydrogen, methyl, chloro, bromo, trifluoromethyl or difluoromethoxy.

6. A compound according to claim 5 wherein t is zero, Z is in the meta or the para position and Z is chloro or trifluoromethyl.

7. The compound ethyl 3-(3-chlorobenzyloxycarbonylamino)-2-butenoate, according to claim 6.

8. The compound ethyl 3-(3-trifluoromethylbenzyloxycarbonylamino)-2-butenoate, according to claim 6.

9. A compound according to claim 5 wherein t is one, Y is in the meta position, Z is in the para position, and each of Y and Z is independently chloro or trifluoromethyl.

10. The compound ethyl 3-(3,4-dichlorobenzyloxycarbonylamino)-2-butenoate, according to claim 9.

* * * * *